United States Patent [19]

Shah et al.

[11] Patent Number: 5,714,543
[45] Date of Patent: Feb. 3, 1998

[54] WATER SOLUBLE POLYMER ADDITIVES FOR POLYURETHANE-BASED PRESSURE SENSITIVE ADHESIVES

[75] Inventors: Kishore R. Shah, Bridgewater; Tak-Lung Chang, Skillman; Agis Kydonieus, Kendall Park, all of N.J.

[73] Assignee: Bristol-Myers Squibb Company, Skillman, N.J.

[21] Appl. No.: 180,598

[22] Filed: Jan. 13, 1994

[51] Int. Cl.$^6$ ............................................. C08L 75/00
[52] U.S. Cl. ................................. 525/123; 525/453
[58] Field of Search .............................. 525/123, 453

[56] References Cited

U.S. PATENT DOCUMENTS

| | | | |
|---|---|---|---|
| 3,437,622 | 4/1969 | Dahlet et al. | 528/77 |
| 3,743,617 | 7/1973 | Kest | 525/453 |
| 3,789,053 | 1/1974 | Clarke | 525/453 |
| 4,338,239 | 7/1982 | Dammann | 524/549 |
| 4,497,914 | 2/1985 | Allen et al. | 523/105 |
| 4,820,745 | 4/1989 | Müller et al. | 522/90 |
| 4,888,379 | 12/1989 | Henning et al. | 524/500 |
| 5,169,468 | 12/1992 | Royce et al. | 156/234 |
| 5,509,913 | 4/1996 | Yeo | 604/364 |

OTHER PUBLICATIONS

Hawley's Condensed Chem. Dictionary; 1987; p. 947.

*Primary Examiner*—Rachel Gorr
*Attorney, Agent, or Firm*—Theodore R. Furman, Jr.; John M. Kilcoyne

[57] ABSTRACT

In accordance with the present invention novel polyurethane PSAs containing water soluble polymer additives have enhanced water uptake. The water soluble polymer additives suitable for use herein have a solubility parameter in poorly hydrogen-binding solvents (e.g., hexane, cyclohexane and the like) in the range of from 8–10. The water soluble polymers must also be free from moieties which will react with isocyanates. Such PSAs retain their transparency and peel strength characteristics and can still be employed as relatively thin films (i.e., 2 to 100 mils) while exhibiting only minimal swelling when in contact with moist environments.

11 Claims, 2 Drawing Sheets

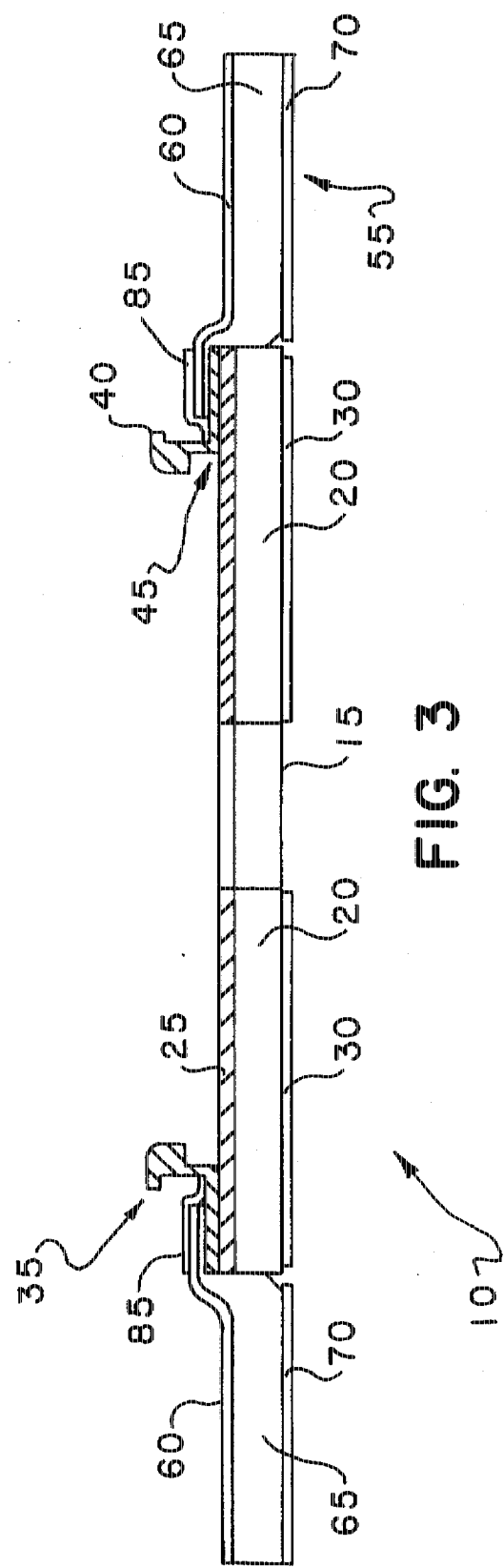

WATER SOLUBLE POLYMER ADDITIVES FOR POLYURETHANE-BASED PRESSURE SENSITIVE ADHESIVES

This invention relates to polyurethane-based pressure sensitive adhesives ("PSAs") including certain water soluble polymer additives to enhance water uptake, and is more particularly concerned with medical products utilizing such PSAs wherein the properties of the adhesive is not adversely affected by the polymer additives.

BACKGROUND OF THE INVENTION

Until the early 1950's commonly used pressure sensitive adhesives ("PSAs") for skin applications were based on natural or synthetic rubber compositions compounded with low molecular weight tackifiers, plasticizers, stabilizers, etc. These adhesives had the disadvantage of being quite hydrophobic and incapable of absorbing water. Thus, such adhesives would trap water under the covered area, often causing skin maceration or other skin damage. Furthermore, the low molecular weight ingredients compounded into these adhesives often would penetrate the skin, causing irritation or sensitization.

Polyacrylate PSAs are an improvement over the rubber-based adhesives, partly due to their self-adhesive property. This property allows them to be prepared as single-component polymeric materials without the need for potentially allergenic modifying or tackifying agents. However, these adhesives often contain unreacted residual acrylic monomer as an impurity in an amount which would irritate and/or sensitize skin. Although these polyacrylate PSAs are much more permeable to moisture or water vapor than are the rubber-based adhesives, they are incapable of absorbing any significant amounts of moisture or water. Therefore, when used for long duration in skin or wound care applications, adhesion is compromised and/or skin damage or maceration may result.

One variation of these polyacrylate PSAs is disclosed in U.S. Pat. No. 4,914,173 to Ansell. The specific PSAs of that patent are obtained by reacting an isocyanate prepolymer, which is the reaction product of a poly-functional isocyanate and a polyoxyalkylene diol monoalkyl ether, with a hydroxy-containing ester of acrylic or methacrylic acid to form a polymer and then cross-linking the polymer by irradiation to form a PSA that is not self-adherent but is capable of absorbing up to 95% by weight of water when hydrated. Although useful in applications where the adhesive will contact a moist or wet environment, these adhesives do not have sufficient tack or initial adhesive properties to be adherent to the skin for certain uses.

An advance in PSA formulation for skin and particularly for wound care applications was the development of compositions comprising blends of one or more water-soluble or swellable hydrocolloids and a tacky, viscous, polymeric material such as polyisobutylene as disclosed in Chen U.S. Pat. No. 3,339,546. Another example is Doyle et al., U.S. Pat. No. 4,551,490, which discloses medicinal grade pressure sensitive compositions containing polyisobutylenes or blends of polyisobutylenes and butyl rubber, a styrenic radical or block type copolymer, mineral oil and water soluble hydrocolloid gum and a tackifier. Such hydrocolloid containing PSAs have the advantage of providing the desired adhesion to skin and, at the same time, are capable of absorbing transepidermal water loss (i.e., perspiration) or other body fluids, including wound exudates.

Hydrocolloid containing PSAs have found use in medical applications such as ostomy devices and wound dressings, where the adhesives maintain the device on skin for several days without skin damage. However, existing hydrocolloid PSAs have substantial limitations in that they are opaque, lack quick initial tack, and tend to disintegrate upon excessive water absorption.

Polyurethanes are polymeric products of diols or polyols and diisocyanates or polyisocyanates. Despite the broad applications of polyurethane chemistry, polyurethane based PSAs are not widely used and to date have been found suitable for only a few specialized applications. A suitable balance of elastic and viscous properties which is required in a PSA has not been readily attainable in conventional polyurethane materials.

Existing polyurethane based adhesives function either as weak elastics or simply as high viscosity liquids. The adhesives composed of the elastic type polyurethanes tend to fail by gradually peeling away from surfaces to which they have been applied. The high viscosity type polyurethanes, which are typically obtained by using a substantial excess of polyol, leave a residue upon removal, and their cohesive strength is too low to withstand the stresses applied in many applications.

The difficulty of attaining this balance of viscoelastic characteristics in a polyurethane explains the paucity of prior art polyurethane PSA literature. Allen et al., U.S. Pat. No. 4,497,914, discloses an ostomy gasket adhesive comprised of a polyurethane prepared by reaction of an organic polyisocyanate with one or more di or polyfunctional hydroxyl compounds, for example, polyols derived from propylene or ethylene oxide, in which is incorporated a hydrophilic filler, such as a cellulosic or natural gum. The adhesive is capable of absorbing bodily fluids by virtue of dispersed hydrophilic filler physically encapsulated within the self-sustaining polyurethane adhesive composition.

Muller et al. U.S. Pat. No. 3,930,102 discloses the preparation of a webstock having a self-adhesive polyurethane coating produced by the reaction of a trifunctional propylene oxide based polyol and an aliphatic diisocyanate employing an NCO/OH ratio in the range of 0.71 to 0.85. This type of webstock is said to be suitable for the production of labels and tapes. However, these compositions are not sufficiently hydrophilic to allow absorption of bodily fluids.

A need thus exists for polyurethane pressure sensitive adhesives for skin application which have adequate moisture absorption or permeation capacities and have other desired properties, such as transparency, conformability to body shape, quick tack, adhesive strength tailorable to the application, high wet strength, and lack of cold flow.

Copending application U.S. Ser. No. 973,448, entitled "Polyurethane Pressure Sensitive Adhesives," filed Nov. 9, 1992, issued as U.S. Pat. No. 5,591,820 discloses a novel class of polyurethane-based pressure sensitive adhesives (PSAs) which exhibit a high degree of water absorption and/or water vapor transmission capabilities. Specifically, these PSAs comprise a polyurethane polymer having excess hydroxyl functionality, a glass transition temperature of less than about 0° C., a moisture absorption at equilibrium of at least about 70% of its weight and/or a moisture vapor transmission rate of at least about 300 grams/meter$^2$/24 hours at 37° C. and 90% relative humidity. These properties provide that such PSAs are ideally suited for medical uses including, but not limited to, ostomy devices, wound dressings, and the like. In addition to these desirable hydrophilic and vapor transmission qualities, the above polyurethane based adhesives have good peel strength and provide a desirable thin, transparent adhesive film.

Incorporation of hydrocolloids, or water soluble polymers (hereinafter "water soluble polymers"), into such adhesives to enhance moisture uptake has been previously found to sacrifice the desirable characteristics of the polyurethane-based PSAs. For example, incorporation of sodium carboxymethylcellulose or pectin renders the films opaque and may result in a substantial degree of swelling in moist environments.

Additives for use in polyurethane-based PSAs which will enhance water uptake without adversely affecting the PSA would be a useful addition to the art.

SUMMARY OF THE INVENTION

In accordance with the present invention novel polyurethane PSAs containing water soluble polymer additives have enhanced water uptake. The water soluble polymer additives suitable for use herein have a solubility parameter in poorly hydrogen-binding solvents (e.g., hexane, cyclohexane and the like) in the range of from 8–10. The water soluble polymers must also be free from moieties which will react with isocyanates. Such PSAs retain their transparency and peel strength characteristics and can still be employed as relatively thin films (i.e., 2 to 100 mils) while exhibiting only minimal swelling when in contact with moist environments.

BRIEF DESCRIPTION OF THE DRAWING

FIG. 3 is an enlarged cross-sectional view of the gasket of FIGS. 1 and 2.

DETAILED DESCRIPTION OF THE PREFERRED EMBODIMENTS

Figure 1:
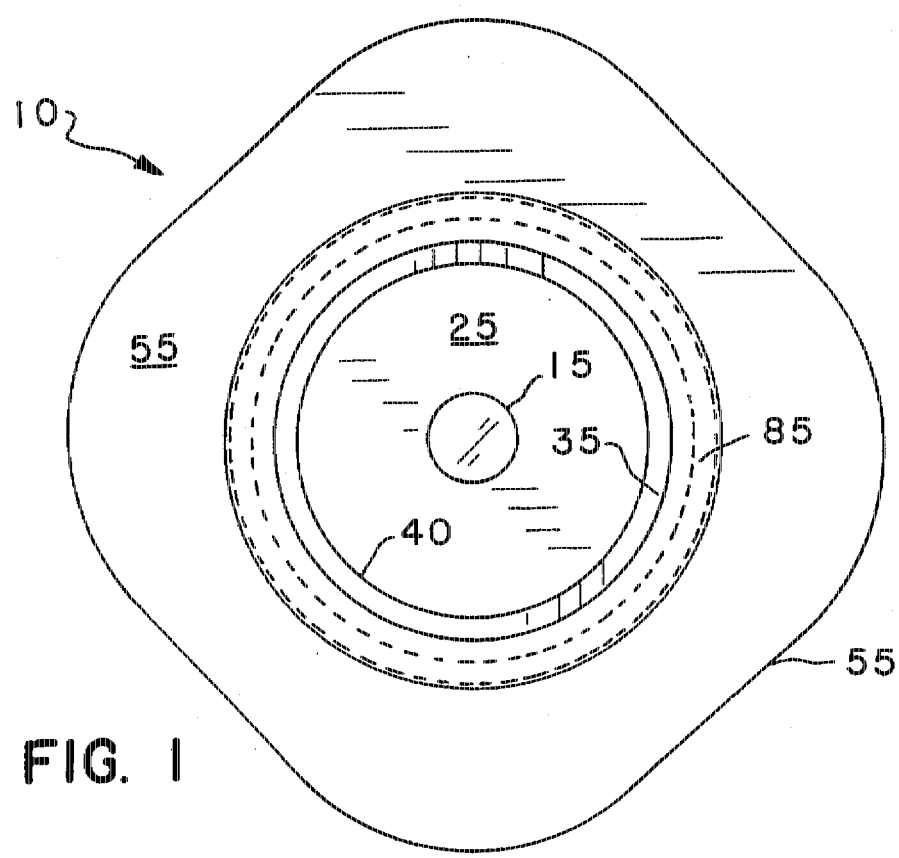
FIG. 1 is a front view of an ostomy gasket which includes a PSA band in accordance with the invention.

It has now been found that the class of water soluble polymers having a solubility constant in the range of from 8 to 10 and free from moieties which will react with isocyanate groups are excellent additives to polyurethane PSAs, in that the integrity and desirable characteristics of the PSA film are maintained while providing enhanced water uptake. This class of water soluble polymers is chosen so as to be substantially miscible in both the polyol and isocyanate components which are used to prepare the polyurethane PSA. Indeed, the preparation of the present PSAs involves, inter alia, dissolving a desired water soluble polymer in either the polyol or isocyanate component and thereafter reacting the components to form the corresponding polyurethane PSA. For example, the water soluble polymer is preferably dissolved into a polyol solution containing a catalyst prior to reaction with the isocyanates. Thereafter, the so-formed premixture is reacted with isocyanates, preferably in an NCO/OH mole weight ratio of from about 0.5/1 to about 0.99/1 to provide a clear adhesive.

Typical water soluble polymers having a solubility constant in the range of from 8 to 10 include poly(2-ethyl-2-oxazoline), poly(vinylmethylether) and the like. Most preferred is poly(vinylmethylether) commercially available from BASF as Lutonal M-40. In accordance with this invention, the water soluble polymers can be added to the polyurethane PSA in amounts corresponding to the degree of water uptake desired in the final product. Typically the polymers are present in a range of from about 1 to about 40% by weight of the PSA formulation. Preferred adhesives contain about 25 to 35% by weight of the water soluble polymer and most preferred adhesives contain about 30% by weight.

The water soluble polymer additives having a solubility constant in the range of from 8 to 10 can be added to any polyurethane-based PSA to enhance water uptake. These additives are ideally suited for incorporation into the polyurethane adhesives disclosed in copending U.S. Ser. No. 973,448, issued as U.S. Pat. No. 5,591,820, mentioned above.

Thus, preferably the pressure-sensitive adhesives comprise a polyurethane polymer having excess hydroxyl functionality, a glass transition temperature of less than about 0° C., a moisture absorption at equilibrium of at least about 20% of its weight and/or a moisture vapor transmission rate of at least about 300 grams/meter$^2$/24 hours measured at 37° C. and a 90% relative humidity gradient. Advantageously, the glass transition temperature of the polymer is less than about –30° C., the moisture absorption at equilibrium of at least about 100% of its weight and/or the moisture vapor transmission rate is at least about 500 grams/meter$^2$/24 hours. These polymers provide a peel adhesion to human skin of between about 0.3 and 4 and preferably between about 0.5 and 3.5 newtons/cm width of the polymer.

Preferably, the polyurethane polymer is formed by the reaction of an isocyanate component and a polyol component at a molar ratio of isocyanate moieties to hydroxyl moieties of less than one with at least one of the components having a functionality that is greater than two to facilitate crosslinking. The polymer is crosslinked to a crosslink density alpha ($\alpha$) defined by the equation $$\alpha = \frac{\sum_{i=1}^{n} X_i(F_i - 2)}{(1.05 - r)Mw}$$

wherein i=1 to n where n is the number of the reactant components $X_i$=mole fraction of $i_{th}$ component $F_i$=functionality of the $i_{th}$ component r=the NCO/OH molar ratio Mw=Molecular weight of the polyol of between about $10^{-4}$ and $10^{-3}$ to obtain the desired properties. When the isocyanate component is an aliphatic polyisocyanate, the crosslink density is preferably between about $2\times10^{-4}$ and $10^{-3}$, while for aromatic polyisocyanates the crosslink density is preferably between about $4\times10^{-4}$ and $9\times10^{-4}$.

A preferred molar ratio is between about 0.5 and 0.99, and more preferably between about 0.65 and 0.99, and most preferably between about 0.85 and 0.99. The polyol component advantageously comprises a polyether polyol having a molecular weight of between about 1000 and 10,000, such as a homopolymer or copolymer containing ethylene oxide or propylene oxide groups. The polyol component may also be a hydroxyl terminated prepolymer. When moisture absorbent adhesives are desired, the polyol component can be a polyether diol or triol containing at least about 30% by weight or ethylene oxide groups.

The isocyanate component has a functionality of equal to or greater than 2, and may be an aliphatic polyisocyanate, an aromatic polyisocyanate or combinations thereof. Also, the isocyanate component may be an isocyanate terminated prepolymer. As noted, at least one of the isocyanate or polyol components must have a functionality of greater than 2 to obtain the desired crosslinking of the polymer.

The invention also relates to a medical article or device for application to skin which comprises a layer of the pressure-sensitive adhesive described above and a backing material in contact with at least a portion of one side of the layer. The backing material in contact with at least a portion of one side of the layer. The backing material may be a natural or synthetic fiber, a woven or non-woven fabric, paper or a thermoplastic polymer. Also, a release layer in contact with the side of the pressure-sensitive adhesive layer in contact with the side of the pressure-sensitive adhesive layer opposite the backing material may be included to protect the adhesive prior to use. Thus, the release layer comprises a material that does not permanently bond to the pressure-sensitive adhesive layer, such as a silicone coating.

This medical article may also include a backing layer and a layer of the pressure sensitive adhesive described above on at least a portion of one side of the backing layer for contacting the skin and securing the article thereto. This article advantageously includes a moisture or water absorbent material positioned for placement upon a moist or wet environment, wherein the pressure sensitive adhesive layer is located adjacent at least a portion of the absorbent material. If the absorbent material is in the form of a disk, the pressure sensitive material layer may be associated with and at least partially surround the perimeter of the disk. A support layer may be provided for the absorbent material such that the pressure-sensitive adhesive layer is attached onto at least a portion of the periphery of the support layer and surrounds the entire perimeter of the disk.

In another embodiment, the medical article further comprises an attachment member for connection to another medical device, such as a bag or container. Thus, the disk would include an aperture therein to permit passage of a fluid therethrough. To provide a secure attachment to the patient and to prevent leakage, means for joining the pressure-sensitive adhesive layer to the support layer may be used, such as an ultrasonic weld.

Accordingly, the medical article or device of the invention may be provided in the form of an ostomy device, a wound dressing, a medical tape, a bandage, an incontinence device, a dermatological device, a transdermal device, a surgical incise drape or an intravenous catheter securement device.

Another embodiment of the invention relates to a method for making a pressure-sensitive adhesive for application to skin which comprises premixing the desired water soluble polymer into either the isocyanate component or the polyol component and then providing a mixture of the isocyanate component and the polyol component at a molar ratio of isocyanate moieties to hydroxyl moieties of less than one; selecting at least one of the components to have a functionality that is greater than two to facilitate crosslinking and reacting the isocyanate and polyol components in the presence of a catalyst to form a polyurethane polymer having a glass transition temperature of less than about 0° C., a moisture absorption at equilibrium of at least about 20% of its weight and/or a vapor transmission rate of at least about 300 grams/meter$^2$/24 hours measured at 17° C. and a 90% relative humidity gradient.

The mixture may be cast upon a substrate and heated at a sufficient temperature of between about 100° and 150° C. and for a sufficient time of between about 1 to 25 minutes to form a layer of the polymer. This layer may be provided upon a backing material or a release layer and would possess a peel adhesion to human skin of between about 0.3 and 4 and preferably between about 0.5 and 3.5 newtons/cm width of the polymer.

Preferably, a polyol component is a polyol having a molecular weight of from about 1,000 to about 10,000 or mixtures of such polyols, with an isocyanate such as a polyisocyanate. Although any of a wide variety of polyols can be used, those which are not crystalline are the most suitable. Exemplary polyols include polyether diols or triols (ethylene oxide and propylene oxide polymers and copolymers) such as those available from Olin (e.g., the Poly G series). In general, for comparable formulations, the higher molecular weight polyols would provide greater peel strengths in the resulting adhesive.

Where increased moisture or water absorption properties are desired in the PSA, polyols that contain a significant amount of polyoxyethylene are used so as to increase the hydrophilic character of the polymer. These polyols should contain at least about 30% of polyoxyethylene in order to enable the polymer to absorb water in an amount of at least about 20% of its weight and as high as 400 to 1000%.

Typical polyols which are useful for this embodiment include Dow Chemical's XUS15176 and the various commercial Carbowaxes which are available in a range of molecular weights from the Union Carbide Corporation. Representative Carbowaxes are PEG (Carbowa 1450) and PEG (Carbowax 8000) in which the numbers refer to molecular weights. The proportion of polyoxyethylene which is present in the polyol will determine the degree of hydrophilic character of the polyurethane. Increasing the amount of polyoxyethylene promotes strong hydrophilic properties to the final product, while a lessened hydrophilic character results by increasing the proportion of polyoxypropylene in the polyol.

The functionality of the polyol that is used is at least 2 and usually is greater than 2, with the higher functionalities providing increased crosslinking of the polyurethane. A number of polyols which are suitable when used alone or in combination are listed below in Table 1.

The isocyanates which may be used in making the polyurethanes of the PSAs of the invention may be represented by R(NCO)n wherein n is at level 2 and preferably between about 2 and 4, and R is an aliphatic, alicyclic, aliphatic-alicyclic, aromatic, or aliphatic-aromatic hydrocarbon compound ranging from about 4 to 26 carbon atoms, but more conventionally from about 6 to 20 and generally from about 6 to 13 carbon atoms.

TABLE 1

| Component | Functionality | Equivalent | ETO % | Supplier |
|---|---|---|---|---|
| SUITABLE POLYOLS | | | | |
| POLY G | | | | |
| 55-28 | 2 | 2025.00 | 30 | OLJN |
| 55-37 | 2 | 1512.00 | 30 | OLJN |
| 55-56 | 2 | 976.00 | 45 | OLJN |
| 76-120 | 3 | 457.00 | 30 | OLJN |
| 83-34 | 3 | 1576.00 | 70 | OLJN |
| 85-28 | 3 | 2025.00 | 10 | OLJN |
| 85-36 | 3 | 1508.00 | 17 | OLJN |
| Voranol | | | | |
| 5148 | 3 | 2357.00 | 19 | DOW |
| 5287 | 2 | 1018.00 | 12 | DOW |
| 5471 | 3 | 1603.00 | 14 | DOW |
| Voran | | | | |
| 220-037 | 2 | 1500.00 | 0 | DOW |
| 232-034 | 3 | 1636.00 | 14 | DOW |
| 240-446 | 4.5 | 125.10 | 0 | DOW |
| 240-800 | 4 | 69.70 | 0 | DOW |
| 270-370 | 7 | 155.90 | 0 | DOW |
| XUS 15176.00 | 2 | 1500.00 | 30 | DOW |
| Multranol 3400 | 3 | 1000.00 | 0 | MOBAY |
| Multranol 3901 | 3 | 1997.00 | 0 | MOBAY |
| Multranol 9133 | 3 | 53.95 | 0 | MOBAY |
| Desmofen 2500 | 2 | 505.00 | 0 | MOBAY |
| Quadrol | 4 | 73.00 | 0 | MOBAY |

TABLE 1-continued

SUITABLE POLYOLS

| Component | Functionality | Equivalent | ETO % | Supplier |
|---|---|---|---|---|
| Carbowax | | | | |
| 1450 | 2 | 714.00 | 100 | CARBIDE |
| 3350 | 2 | 1638.00 | 100 | CARBIDE |
| 4600 | 2 | 2352.00 | 100 | CARBIDE |
| 8000 | 2 | 4141.00 | 100 | CARBIDE |
| Terathane | | | | |
| 1000 | 2 | 500.00 | 0 | DUPONT |
| 2000 | 2 | 1024.00 | 0 | DUPONT |
| Pluracol 380 | 3 | 2235.00 | 0 | BASF |
| Poly THF ER 1250 | 2 | 625.00 | 0 | BASF |
| Fomrez | | | | |
| EPD-56 | 2 | 1041.00 | 45 | WITCO |
| EPD-28 | 2 | 2086.00 | 45 | WITCO |
| K22-170 | 6 | 308.00 | 90 | WITCO |
| L49-28 | 3 | 1990.00 | 25 | WITCO |
| ECFL1000Y | 3 | 278.00 | 90 | WITCO |
| Witconl Peg1000L | 2 | 505.00 | 90 | WITCO |

Representative examples of diisocyanates include aliphatic isocyanates such as tetramethylene diisocyanate, hexamethylene diisocyanate, trimethylhexamethylene diisocyanate, dimer acid diisocyanate, isophorone diisocyanate, diethylbenzene diisocyanate, decamethylene 1,10-diisocyanate, cyclohexylene 1,2-diisocyanate and cylohexylene-1,4-diisocyanate and the aromatic isocyanates such as 2,4 and 2,6-tolylene diisocyanate, 4,4-diphenylmethane diisocyanate, 1,4-naphthalene diisocyanate, dianisidine diisocyanate, toluidine diisocyanate, m-xylylene, diisocyanate tetrahydronaphthalene-1,5-diisocyanate, and bis(4-isocyanatophenyl)methane.

Polymeric polyisocyanates having a functionality of greater than 2, such as neopentyl tetraisocyanate, can also be used. A number of suitable isocyanates are listed in Table 2 below. In addition, mixtures of di- and tri-functional isocyanates are commercially available and may be used to obtain an isocyanate component having a functionality of between 2 and 3, while mixtures of tri- and tetra-functional isocyanates may be used to obtain functionalities of between 3 and 4 (i.e., DESMODUR N 3300 from Miles, Perkasie, Pa.). These tri- and tetra-functional isocyanates are illustrated below.

TABLE 2

SUITABLE ISOCYANATES

| Component | Functionality | Equivalent | Supplier |
|---|---|---|---|
| PAPI 94 | 2.2 | 131.50 | DOW |
| PAPI 2580 | 3 | 139.60 | DOW |
| ISONATE 2181 | 2 | 182.60 | DOW |
| ISONATE 2125m | 2 | 125.50 | DOW |
| MONDUR MR | 2.7 | 131.00 | MOBAY |
| MONDUR CD | 2 | 143.00 | MOBAY |
| MONDUR CB75 | 3 | 323.00 | MOBAY |
| DESMODUR W | 2 | 132.00 | MOBAY |
| TMXDI | 2 | 122.10 | CYANAMID |
| CYTHANE 3160 | 3 | 404.00 | CYANAMID |
| TDI 80 | 2 | 87.00 | OLIN |
| DMI 1410 | 2 | 295.77 | HENKEL |

Desmodur N 3300 has a functionality of about 3.4–3.6 and it is a mixture of the two isocyanates depicted above. This isocyanate compound is preferred from the standpoint of toxicity because it is an aliphatic isocyanate derivative that produces a non-toxic degradation product. Furthermore, the isocyanate compounds shown above can be mixed together or with the diisocyanates mentioned above to attain the desired functionality of the isocyanate component.

Generally speaking, the polyurethane is prepared from about 75% to 95% of the polyol, and about 5% to 25% of the polyisocyanate. The relative amounts are selected so that the NCO/OH ratio is between about 0.5 and 0.99 and preferably between about 0.65 to 0.99, so that these polyurethanes have excess hydroxyl functionality.

In preparing the polyether polyurethane adhesives of this invention, the polyols and the polyisocyanates are reacted in the presence of known catalysts for such reaction, for example, tin salts and organic tin esters such as dibutyltin dilaunate and stannous octoate. An advantageous catalyst is METACURE T-12 by Air Products and Chemicals, Inc., because this catalyst has been approved by the FDA for medical application and provides a satisfactory reaction.

Also, it is preferred for the pressure-sensitive adhesive to have a glass transition temperature (Tg) of less than 0° C. and preferably less than $-30°$ C. Thus, the amount of crystalline polyol used, if any, should be held to a minimum. By choosing polyols which are not crystalline or do not crystallize, or which do not cause phase separation during reaction, a transparent, uncolored polymer is obtained. A colored polymer is also avoided by selecting isocyanate and polyol components which form polymerization products that do not contain multiple bonds which would be capable of absorbing light or heat energy and undergo transformations resulting in colors.

The pressure-sensitive polyurethane adhesives of this invention each have an MVTR (at equilibrium) of at least 300 and preferably greater than 500 $g/m^2/day$ when measured at 37° C. and a 90% relative humidity gradient. When these adhesives are applied onto skin, the skin can "breathe," such that any excess moisture generated by perspiration of the skin can pass through the adhesive to prevent deterioration of the skin, while some moisture is retained to provide an environment which promotes healing.

In copending application U.S. Ser. No. 973,448, entitled "Polyurethane Pressure Sensitive Adhesives" filed Nov. 9, 1992, issued as U.S. Pat. No. 5,591,820, it has been disclosed that the polyurethane adhesive peel strength, for a given backing and at a given adhesive thickness, is a function of the extent of crosslinking which, in turn, depends upon the functionality of the components used to form the polyurethane polymer. The extent of crosslinking can be expressed as the number of crosslinks per unit weight. With a greater extent of crosslinking, the peel adhesion becomes lower, such that peel adhesion has been found to be inversely related to the extent of crosslinking.

It was further found that this crosslink density is a function of an interplay of molecular parameters of the polyurethane components. A mathematical relationship incorporating these components has been derived to define the optimum combination of the kind and proportions of the components which results in the formation of polyurethane PSAs for the specified medical uses. This relationship can be used to calculate a value, designated as $\alpha$, which is representative of the extent of crosslinking of the polymer. Thus, the $\alpha$ value, which is based on the average functionality of the reactants, the NCO/OH mole ratio, and the molecular weight of the polyol, may be used as a measure of the performance of one polymer relative to another, as well as to select which polymers are useful in accordance with the teachings of the present invention.

The following expression sets forth the relationship between the variables which is used to calculate α. As noted above, the peel strength is inversely proportional to the extent of crosslinking which can be expressed as follows:

$$\text{Desired Peel Strength} = \frac{K}{\text{number of crosslinks/unit weight of polymer}}$$

wherein the number of crosslinks/units weight of polymer is proportional to α as calculated by the following formula:

$$\alpha = \frac{\sum_{n}^{i=1} X_i(F_i - 2)}{(1.05 - r)Mw}$$

wherein
i=1 to n where n is the number of the reactant components
$X_i$=mole fraction of $i_{th}$ component
$F_i$=functionality of the $i_{th}$ component
r=the NCO/OH molar ratio
Mw=Molecular weight of the polyol.

Thus, in a given polyurethane formulation, an interplay of different parameters governs the peel strength of the adhesive.

An α value in the range of $10^{-4}$ to $10^{-3}$ is representative of an adhesive which has the desired balance of cohesive and adhesive characteristics which are typically required for a pressure-sensitive adhesive, with α values of between $2 \times 10^{-4}$ and $10^{-3}$ for aliphatic polyurethanes and between 4 and $9 \times 10^{-4}$ for aromatic polyurethanes being particularly advantageous.

Accordingly, based upon this information, one skilled in the art can routinely select the particular isocyanate and polyol components and molar ratios thereof to obtain polyurethane polymers which have α values which fall in the desired ranges. In addition, the α value can be calculated prior to actual formulation of the polymer, so that the experimental work is necessary only after selecting those components and molar ratios which provide α values in the desired range.

The pressure-sensitive adhesive products of this invention are prepared by coating a mixture of the polyurethane adhesive components on a backing material and allowing the polyurethane components to cure. Useful backing materials are thermoplastic elastomers such as polyurethane film, plasticized PVC, breathable woven or non-woven fabrics made of natural or synthetic fibers such as polyester and porous paper. The adhesive components can also be applied to a release liner such as mylar film with a silicone coating and silicone coated paper and then after curing removed and placed on a backing material. The thickness of the adhesive coating is about 1 to 60 mils depending upon the requirements of the specific product application, while the backing material has a thickness in the range of between about 0.5 and 5 mils and typically about 1–2 mils.

The above-described polyurethane pressure-sensitive adhesives are particularly useful for attaching medical devices and other materials to the skin. The adhesives can be used as or applied to bandages, ostomy devices, incontinence devices, incise drapes, intravenous catheter holders, transdermal drug delivery devices and medical tapes such as wound closure tapes. Where absorbent adhesives are desired, such as in wound dressings, the polymers that have high water absorption properties can be successfully used. Because of the skin adhesion properties of these PSAs, i.e., no skin irritation or sensitization, and lack of skin or hair adhesion on removal, these adhesives are skin friendly and are very useful in the medical field where skin contact is required.

Figure 2:
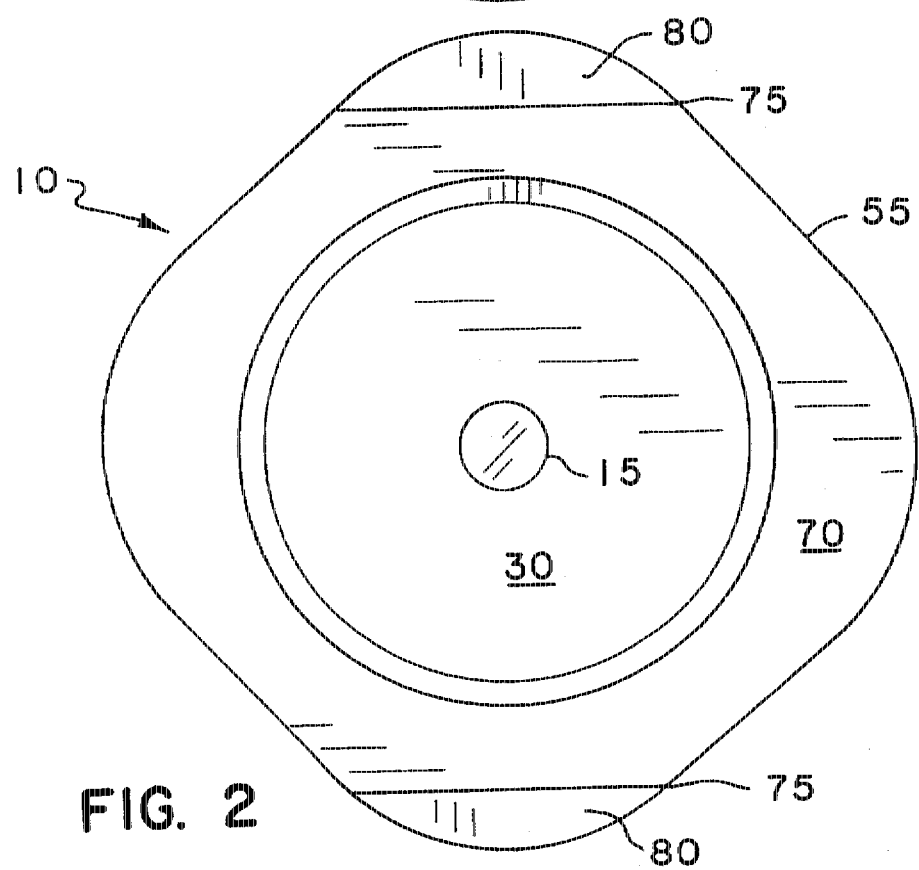
FIG. 2 is a rear view of the gasket of FIG. 1.

FIGS. 1–3 illustrate an ostomy gasket 10 which includes adhesives made of the polymers of the present invention. This device has a central aperture 15 for placement over the incision and through which fluids may drain. Adjacent to and surrounding the aperture 15 is a layer 20 of an adhesive material which has highly absorbent properties to withstand the moist environment and fluids which drain through the aperture. This layer 20 is preferably made of material such as STOMAHESIVE, which is available from ConvaTec, Skillman, N.J. Alternatively, this layer 20 of absorbent material can be of a pressure-sensitive adhesive in accordance with the invention which includes a high ethylene oxide content.

This absorbent material 20 is preferably supported on a polyethylene film 25. When an adhesive material such as STOMAHESIVE or the like is used, the opposite side (or working face) of this layer 20 includes release liner 30 which allows handling of the article without concern as to the absorbent material adhering to unintended surfaces.

The polyethylene film support 25 is secured to a flange 35 which is adapted to receive an ostomy bottle or other container for storing the fluid which passes through aperture 15. Thus, flange 35 includes a lip 40 and corresponding recess 45 to facilitate attachment of the bottle or container thereto. Flange 35 is attached to disk shaped extension 50. A supportive adhesive band 55 in accordance with the invention completely surrounds the periphery of the flange 35. This band 55 includes a polyester fiber backing layer 60 upon which is placed an adhesive of the present application. This adhesive is shown as 65. To prevent the adhesive from sticking to surfaces prior to the desired time of use, a release layer 70 is provided on the side opposite the backing layer (i.e., the adhesive face). As shown in FIG. 2, the backing layer includes cut notches 75 to facilitate removing a portion of the backing 80 and thus more easily expose the adhesive face for attachment to the desired surfaces.

Adhesive band 55 is attached to the top of flange extension 50 and adhered thereto due to the adhesive properties of layer 65. To obtain a more secure connection between band 55 and flange portion 50, a plastic ring 85 is placed upon the backing member 60 of the band 55 and is ultrasonically welded to extension 50 of flange 35.

When the device is to be used, the release layers 70 and 30 are first removed thus exposing the PSA material 65 of band 55 and the absorbent material 20. The PSA material 65 as noted above is skin friendly and provides a secure bond to the skin without damaging it. Thus, the gasket is retained in the desired place despite whether absorbent layer 20 has adhesive characteristics or not. When absorbent layer 20 is made of a highly water absorbent material, it most often does not develop sufficient tack or peel strength so that it can be properly secured in place on the patient. Thus, the PSA adhesive 65 provides a secure bonding of the gasket to the patient and holds the absorbent layer in place so that any further bonding due to the adhesive properties of absorbent 20 can occur over time. Again, as noted above, PSA layer 65 allows the skin to breathe so that excessive fluid does not accumulate thereon and cause damage or other detrimental affects to the skin.

The following examples, which are intended to illustrate the invention described herein without unduly restricting it, provide further illustrations of how to select the appropriate components and amounts thereof to form the desired pressure-sensitive adhesives.

EXAMPLE 1

Hydrophobic Polyurethane Adhesive With 29% Loading of Polyvinyl Methyl Ether (Lutonal M40)

A homogeneous polyol-Lutonal M40 solution was prepared by dissolving 28.8 parts of polyvinyl methyl ether (Lutonal M40 from BASF) in a 64.5 parts of heated (80° C.) polyol (Poly G 26-37 from Olin Chemicals) solution containing 0.2 part of T-12 catalyst (dibutyl tin dilaurate from Air Products) with stirring for at least two hours. The resulting polyol-Lutonal M40 solution is then dried under vacuum in order to remove moisture. To this clear solution, 4.3 parts of N-3300 multi-functional hexamethylene isocyanate prepolymers and 2.2 parts of DESMODUR W, methylene bis(cyclohexyl-4-isocyanate), (both isocyanates from Miles Inc.) are added at 60° C. in one portion. The reaction mass is then casted onto a support film with desired thickness. After completion of the casting, the casted material is cured in an air circulating oven at 100° C. for 60 minutes. After cooling to room temperature, a clear and pressure-sensitive adhesive slab is obtained for further testing on its physical properties.

EXAMPLE 2

Hydrophobic Polyurethane Adhesive With 23% Loading of Polyvinyl Methyl Ether (Lutonal M40)

The same procedure as in Example 1 was used to prepare the 23% loading sample except that the amount of each ingredient used in the preparation are changed to reflect the loading and NCO/OH ratio changes: 22.6 parts of Lutonal M40, 70.0 parts of Poly-G 26-37, 4.3 parts of N-3300, 2.9 parts of DESMODUR W, and 0.2 part of T-12.

EXAMPLE 3

Hydrophobic Polyurethane Adhesive Without Polyvinyl Methyl Ether

A polyol solution is prepared by mixing 91.6 parts of hydrophobic polyol (Poly-G 26-37 from Olin Chemicals) and 0.2 part of T-12 catalyst at a room temperature. The resulting clear solution is dried under vacuum. To this solution, 4.0 parts of N-3300 and 4.2 parts of DESMODUR W are added in one portion at room temperature with stirring. After stirring for 10 minutes at 60° C., the reaction mass is then casted and cured by using the same procedure specified in Example 1.

EXAMPLE 4

Hydrophilic Polyurethane Adhesive Without Polyvinyl Methyl Ether

The same procedure as in Example 3 is used to prepare a hydrophilic polyurethane adhesive except that the hydrophobic polyol is substituted with a hydrophilic polyol Poly-G 55-37. The amount for each ingredient are as follows: 99.55 parts of Poly-G 55-37; 0.2 part of T-12 catalyst; 3.38 parts of N-3300; 4.05 parts of DESMODUR W.

Properties of the Skin Barrier Materials

The samples from Examples 1 through 4 were tested as follow:

| Example Number | Lutonal M40 (%) | MVTR* 24–72 hrs $g/m^2/day$ | Water Uptake | Extractables 24 hrs (%) | Extractables 7 days (%) | Swelling | Disintegration |
|---|---|---|---|---|---|---|---|
| 1 | 29 | 879 | 27 | 0.0 | 0.8 | No | No |
| 2 | 22 | 1278 | 10 | 0.0 | 0.6 | No | No |
| 3 | 0 | 2083 | 2 | 0.0 | 0.5 | No | No |
| 4 | 0 | 2170 | 285 | 2.5 | ---- | Yes | No |

*Tested on 2 mil thick samples

Water Vapor Transmission Test

ASTM Standard Test Methods of Water Vapor Transmission of Materials Designation: E96-80 was used. The Water Method paragraph 3.2 of the test method was used.

In the Water Method, a dish is prepared containing distilled water and weighings are made to determine the rate of vapor movement through the specimen from the water to a controlled atmosphere.

What is claimed is:

1. A pressure-sensitive adhesive comprising a polyurethane polymer, resulting from a reaction of a polyisocyanate with a polyol, containing a dissolved water soluble polymer free from moieties which will react with isocyanate groups.

2. The pressure-sensitive adhesive of claim 1 wherein said polymer has a solubility parameter in poorly hydrogen-binding solvents of from about 8 to about 10.

3. The pressure sensitive adhesive of claim 1 wherein said water soluble polymer is poly(vinylmethylether) or poly(2-ethyl-2-oxazoline).

4. The pressure-sensitive adhesive of claim 3 wherein said water soluble polymer is poly(vinylmethylether).

5. The pressure-sensitive adhesive of claim 1 wherein said water soluble polymer is present in an amount of from about 1 to 40% by weight of adhesive.

6. The pressure-sensitive adhesive of claim 5 wherein said water soluble polymer is present in an amount of from about 25 to 35% by weight of the adhesive.

7. The pressure-sensitive adhesive of claim 1 wherein said polyurethane polymer has an excess hydoxyl functionality, a glass transition temperature of less than about 0° C., a moisture absorption at equilibrium of at least about 20% of its weight, and a peel adhesion to human skin of between about 0.3 and 4 newtons/cm width of the polymer.

8. The pressure-sensitive adhesive of claim 7 wherein the glass transition temperature is less than about −30° C., the moisture absorption at equilibrium is at least about 100% of its weight, and the peel adhesion is between about 0.5 and 3.5 newtons/cm width of the polymer.

9. The pressure-sensitive adhesive of claim 1 wherein said polyurethane polymer has excess hydroxyl functionality, a glass transition temperature of less than about 0° C., a moisture vapor transmission rate of at least about 300 grams/meter$^2$/24 hours measured at 37° C. and a 90% relative humidity gradient, and a peel adhesion to human skin of between about 0.5 and 3.5 newtons/cm width of the polymer.

10. The pressure-sensitive adhesive of claim 9 wherein the glass transition temperature of the polyurethane polymer is less than about −30° C., the moisture vapor transmission rate is at least about 500 grams/meter$^2$/24 hours, and the peel adhesion is between about 0.5 and 3.5 newtons/cm width of the polymer.

11. A pressure-sensitive adhesive comprising a polyurethane polymer formed by first dissolving a water soluble polyurethane polymer into a polyol component wherein said water soluble polymer has a solubility constant in poorly hydrogen-binding solvents of from about 8 to 10 and being free from moieties reactive with isocyanates; and the reaction of an isocyanate component and the so-formed polyol component at a molar ratio of isocyanate moieties to hydroxyl moieties of less than or equal to one with at least one of the components having a functionality that is greater than two to facilitate crosslinking, said polymer having a glass transition temperature of less than about 0° C., a moisture absorption at equilibrium of at least about 20% of its weight, and a peel adhesion to human skin of between about 0.3 and 4 newtons/cm width of the polymer.

* * * * *